US009492686B2

(12) United States Patent
Da Silva

(10) Patent No.: US 9,492,686 B2
(45) Date of Patent: Nov. 15, 2016

(54) DEVICES AND METHODS FOR TREATMENT OF SKIN CONDITIONS

(75) Inventor: Luiz B. Da Silva, Danville, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1750 days.

(21) Appl. No.: 11/947,607

(22) Filed: Nov. 29, 2007

(65) Prior Publication Data
US 2008/0139974 A1 Jun. 12, 2008

Related U.S. Application Data

(60) Provisional application No. 60/872,763, filed on Dec. 4, 2006.

(51) Int. Cl.
| A61N 7/00 | (2006.01) |
| A61B 8/00 | (2006.01) |
| A61B 17/00 | (2006.01) |
| A61B 18/00 | (2006.01) |

(52) U.S. Cl.
CPC ............... *A61N 7/00* (2013.01); *A61B 8/546* (2013.01); *A61B 2017/00734* (2013.01); *A61B 2018/00005* (2013.01); *A61N 2007/0056* (2013.01)

(58) Field of Classification Search
USPC ....... 601/2; 607/96; 600/9, 21, 459; 310/311
See application file for complete search history.

(56) References Cited

U.S. PATENT DOCUMENTS

| 4,571,520 A | 2/1986 | Saito |
| 5,213,103 A | 5/1993 | Martin et al. |
| 5,687,729 A * | 11/1997 | Schaetzle ...................... 600/439 |
| 6,049,159 A * | 4/2000 | Barthe et al. .................. 310/334 |
| 6,050,943 A * | 4/2000 | Slayton et al. ............... 600/439 |
| 6,325,769 B1 | 12/2001 | Klopotek |
| 6,500,141 B1 | 12/2002 | Irion |
| 6,595,934 B1 * | 7/2003 | Hissong et al. .................. 601/3 |
| 6,692,450 B1 | 2/2004 | Coleman |

(Continued)

FOREIGN PATENT DOCUMENTS

| DE | 10 2005 001673 | 10/2005 |
| EP | 0 219 988 | 4/1987 |

(Continued)

OTHER PUBLICATIONS

Parthasarthy et al . "Piezo-electric Oscillations of Quartz Plates at Even and Half-odd Harmonics." Nature. 171. (Jan. 31, 1953): 216. Print.*

(Continued)

*Primary Examiner* — Joseph Stoklosa
*Assistant Examiner* — Adam Avigan

(57) ABSTRACT

Devices and methods for the treatment of skin conditions and lesions are disclosed herein. A compact hand held device that can be safely used by those suffering from skin conditions, such as acne, warts, cold blisters, blemished skin, or fine wrinkles. The devices employ the application of ultrasound energy and heat for the treatment of skin conditions and lesions. Typically, the peak temperatures employed are about 40° C. to about 70° C. by the devices, are achieved in less than about 20 second, and maintained for less than about 40 second. Ultrasound absorption and thermal conduction transfers heat from the device to the skin and causes a biological response that accelerates acne clearing, treats blemished skin, itching, or fine wrinkles. The total heat transferred is low enough to prevent burns.

32 Claims, 9 Drawing Sheets

(56) References Cited

U.S. PATENT DOCUMENTS

| | | | |
|---|---|---|---|
| 6,743,222 B2 * | 6/2004 | Durkin et al. | 606/9 |
| 7,195,603 B2 * | 3/2007 | Yamazaki et al. | 601/2 |
| 7,427,273 B2 * | 9/2008 | Mitsui | 601/2 |
| 2002/0082666 A1 | 6/2002 | Babaev | |
| 2003/0060736 A1 | 3/2003 | Martin | |
| 2004/0001809 A1 | 1/2004 | Brisken | |
| 2004/0010222 A1 * | 1/2004 | Nunomura et al. | 604/22 |
| 2004/0039312 A1 | 2/2004 | Hillstead et al. | |
| 2004/0171970 A1 | 9/2004 | Schleuniger | |
| 2005/0075571 A1 | 4/2005 | Barnes | |
| 2005/0154332 A1 * | 7/2005 | Zanelli et al. | 601/2 |
| 2005/0209588 A1 * | 9/2005 | Larson et al. | 606/27 |
| 2005/0240170 A1 * | 10/2005 | Zhang et al. | 606/27 |
| 2006/0074313 A1 * | 4/2006 | Slayton et al. | 600/439 |
| 2006/0084891 A1 | 4/2006 | Barthe et al. | |
| 2006/0089632 A1 * | 4/2006 | Barthe et al. | 606/27 |
| 2006/0111744 A1 * | 5/2006 | Makin et al. | 607/1 |
| 2006/0116671 A1 * | 6/2006 | Slayton et al. | 606/27 |
| 2006/0129214 A1 | 6/2006 | Da Silva et al. | |
| 2006/0271028 A1 * | 11/2006 | Altshuler et al. | 606/9 |
| 2007/0055183 A1 * | 3/2007 | Kaminski et al. | 601/2 |

FOREIGN PATENT DOCUMENTS

| | | |
|---|---|---|
| EP | 1591073 A1 | 11/2005 |
| JP | 2003180843 A | 7/2003 |
| WO | WO 01/17455 | 3/2001 |
| WO | WO 02/094375 | 11/2002 |

OTHER PUBLICATIONS

"Characteristics of piezoelectric Transducers." NDT Resource Center. NDT Resource Center, Dec. 2, 2005. Web. Jul. 17, 2011. <http://web.archive.org/web/20051202111008/http://www.ndt-ed.org/EducationResources/CommunityCollege/Ultrasonics/EquipmentTrans/characteristicspt.htm>.*

Parthasarthy et al . "Piezo-electric Oscillations of Quartz Plates at Even and Half-odd Harmonics." Nature. 171. (Jan. 31, 1953): 216.*

Characteristics of piezoelectric Transducers. NDT Resource Center. NDT Resource Center, Dec. 2, 2005. Web. Jul. 17, 2011. <http://web.archive.org/web/20051202111008/http://www.ndt-ed.org/EducationResources/CommunityCollege/Ultrasonics/EquipmentTrans/characteristicspt.htm>.*

International Search Report for PCT/US2007/086178, mailed May 15, 2008, 6 pgs.

Ed. Steve Webb, the Physics of Medical Imaging, 1988, pp. 337-341.

* cited by examiner

Figure 10 Temperature profile in the transducer ($0.5 \times 10^{-3}$ to 0 meters) and tissue (0 to $-4 \times 10^{-3}$ meters) from t = 0 to t = 20 seconds.

Figure 11 Temperature profile in the transducer ($2\times10^{-3}$ to 0 meters) and tissue (0 to $-4 \times10^{-3}$ meters) from t = 0 to t = 20 seconds.

DEVICES AND METHODS FOR TREATMENT OF SKIN CONDITIONS

STATEMENT OF PRIORITY TO PROVISIONAL APPLICATION

This application claims priority under 35 U.S.C. §119(e) to U.S. Provisional Application No. 60/872,763 filed Dec. 4, 2006.

BACKGROUND OF THE INVENTION

1. Field of the Invention

This invention relates to methods and devices for treating skin conditions using ultrasound.

2. Description of the State of the Art

Acne affects more than 90% of all adolescents, nearly 50% of all adult women and 25% of all adults. One of the main causes of acne is improper drainage of the hair follicle caused by a plug of dead cells or dirt that trap oil and bacteria. The hair follicle opening is approximately 50 μm to about 100 μm in diameter. The opening of any other pore on the skin is substantially smaller. In particular, the opening of a sweat pore is less than about 30 μm in diameter.

There are a variety of ways to treat acne. Benzoyl peroxide is one of the most commonly used ingredients in over-the-counter treatments, and it can be very effective in treating mild cases of non-inflammatory acne. It is safe for children as well as adults, and may be combined with other topical or oral treatments. For patients who suffer from moderate to severe acne, doctors may prescribe a combination of topical remedies and oral antibiotics. The most common oral medications used to treat acne are tetracycline, minocycline, doxycycline and erythromycin.

Alternatives to medication include UV light radiation, laser treatment, or abrasion. Most of these systems are large and in most cases require professional treatment. U.S. Pat. No. 6,635,075 by Li et al. describes a heating device that can also be used to treat acne. The device described in therein uses a heater and temperature sensor to maintain a constant temperature surface that can be applied to skin. In order to prevent burns during the long application time (minutes), the maximum temperature allowed is about 62° C. The long treatment time makes this device impractical for normal acne treatment.

Various ultrasound treatment devices and/or methods for treating tissue have been proposed as discussed in U.S. Pat. No. 6,692,450 to Coleman, U.S. Pat. No. 6,325,769 to Klopotek and references therein. These systems generally use low frequency ultrasound where coupling layers or focusing elements can be placed between the transducer and skin. The use of low frequency ultrasound (<5 MHz) results in deep penetration which is not suitable for treating acne. In addition, these ultrasound systems operate in a linear mode which requires very thin piezoelectric elements which make them delicate and impractical for hand held consumer devices. A need exists for a compact device that can be used effectively and quickly to treat acne. The present invention fulfills this need, and further provides related advantages.

Methods of rejuvenating skin range from the aggressive face lift surgery and skin resurfacing by lasers (for example, using CO2 lasers) or chemical peel, to the less effective non-ablative lasers systems, and RF energy skin rejuvenation systems, microdermabrasion, the use of abrasive devices as well as various lotions and creams. Additional alternative methods include UV, infrared and light radiation, laser treatment, mechanical abrasion or ultrasound energy. Most of these systems are large and in most cases require professional treatment. A need exists for effective skin rejuvenation devices.

SUMMARY OF THE INVENTION

It is an object of the present invention to provide devices and methods for treating skin conditions and skin lesions, such as acne, removing fine wrinkles and clearing skin. Another object of the present invention is to provide a hand held device that can be safely used to heat tissue without causing a burn. These and other objects will be apparent to those skilled in the art based on the teachings herein.

A first aspect of the invention is a device comprising an ultrasound generating element and a controller in a housing, the ultrasound generating element being capable of heating tissue through ultrasound energy absorption and direct thermal transport to a desired peak temperature in a time duration of less than 120 seconds. The peak temperature in tissue produced during the procedure is preferably less than 70° C. to reduce the risk of burns. The ultrasound generating element consists of a piezoelectric element made of ceramic (for example, lead zirconate titanate, PZT) or plastic (polyvinylidine difluoride, PVDF) that can efficiently generate ultrasound energy at a frequency of greater than 5 MHz and less than 50 MHz. The piezoelectric element couples to a backing medium which can be air, foam, or metal. A metal backing medium can be used to conduct heat away from the piezoelectric element and prevent significant heating of the piezoelectric element. In some embodiments, particularly, in embodiments in which thermal heating of the skin directly by the piezoelectric element is to be minimized a cooling element can be integrated into the device. Typically the cooling element cools the piezoelectric element during the procedure; possible cooling elements include thermoelectric coolers and convective cooling of the backing medium.

Another aspect of the invention is methods of use of the devices of the present invention in the treatment of skin conditions, such as acne, warts and skin wrinkles. In a preferred embodiment, the device is used in combination with topical agents used in the treatment of skin conditions. This topical agent can be applied by the user or can be applied with the devices described herein. The present invention can also be combined with acne treatment creams and gels to further accelerate treatment. For example, creams or gels containing benzoyl peroxide could be applied before or after applying the device.

Another aspect of the invention relates to methods for reducing or eliminating hair growth. According to these methods, by the application of focused ultrasonic energy the hair follicle and root can be damaged sufficiently to reduce hair growth.

In one aspect, a device is configured to dissipate heat without substantially interfering or adversely effecting the ability to transmit high-frequency ultrasound energy beneath the skin surface for treatment, without requiring focused ultrasound energy to achieve a therapeutic treatment temperature or delivered thermal energy over time close to the skin surface, e.g., the dermis layer, or just below the epidermis, and without burning the skin surface. In one example, non-focused, or planar ultrasound energy of at least 5 Mhz is used to uniformly heat an area of tissue beneath the skin surface, e.g., about 2 mm below the skin surface, without a significant risk that the skin surface will burn during treatment. This is accomplished by placing the piezoelectric front surface very near, or touching the skin surface while drawing the generated heat away from the front surface of the piezoelectric using a heat sink that is thermally coupled to a rear surface of the piezoelectric. By thermally coupling the heat sink to the rear surface of the piezoelectric (rather than, e.g., placing a heat dissipating solid and/or circulating fluid between the piezoelectric and skin surface), it is possible to heat the area close to the skin surface without a risk that the outer skin surface will burn as a result of the skin being placed adjacent to a heated piezoelectric. As a result, a consumer device, e.g., battery powered, hand-held device, can be used to effectively treat a skin condition just below the skin surface, e.g., about 2 mm below the surface, using greater than 5 Mhz ultrasound energy, without an unacceptable risk of injury to the skin surface.

In some embodiments, an ultrasound device according to the invention may use a matching layer covering the front surface of the piezoelectric. In some embodiments, the matching layer may be planar whereby planar or non-converging acoustic waveforms are transmitted into the skin. In other embodiments, a plurality of focusing lenses may be used when isolated regions of the skin surface are treated. In some embodiments, a topical gel, water or acoustic coupling gel is dispensed from the ultrasound device, or simply manually placed in contact with the surface of the piezoelectric or matching layer covering a piezoelectric in order to remove air gaps. Further, the liquid may be therapeutic and used to both treat a skin condition and eliminate air gaps.

According to one embodiment, a handheld ultrasound device for treatment of a user's skin includes a signal generator configured for generating a driving signal having a frequency of equal to or greater than about 10 Mz and an ultrasound element coupled to the signal generator and adapted for converting the driving signal to a sound wave, the element being tuned to an odd harmonic of the signal frequency.

According to another embodiment, a method for self-treating a skin condition using a consumer hand-held device includes the steps of providing in the hand-held device an ultrasound element having a piezoelectric defining an ultrasound transmitting end, placing, using the one hand, the transmitting end against the skin condition, activating, using the one hand, the piezoelectric while the one hand holds the transmitting end against the skin condition, and removing the transmitting end when a sensory signal is emitted from the hand-held device.

According to another embodiment, a method for therapeutic treatment using an ultrasound device having a transmitting end includes the steps of placing the transmitting end on a skin condition, and treating the skin condition including the step of heating the skin with ultrasonic energy of equal to or greater than about 5 Mhz using planar ultrasonic waves emitted from the transmitting end, such that the skin surface temperature is less than a temperature of skin adjacent to the skin surface.

The ultrasound device may use a piezoelectric having a thickness of about $(2N+1)/2\lambda$ where $\lambda$ is the wavelength of a driving signal applied to the piezoelectric and N is a non-zero integer.

Other objects and advantages of the present invention will become apparent from the following description and accompanying drawings.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
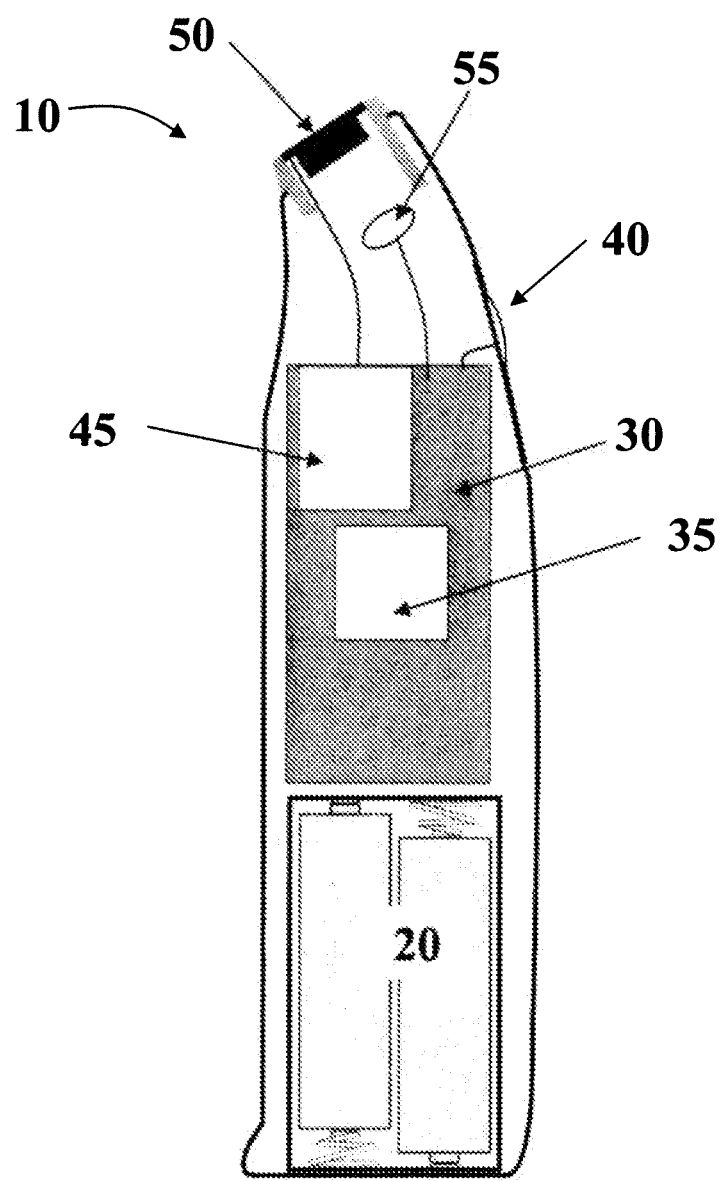
FIG. 1 shows a sectional view of a handheld ultrasound device for treating the skin.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

A compact, hand held device that can be safely used by adolescents and adults suffering from skin conditions and skin lesions, such as acne, blemished skin or fine wrinkles is disclosed. In one embodiment, the device has an on/off switch and a button that activates an ultrasound generating element when the device is placed on the targeted site, e.g., a skin blemish, acne, etc. Activation of the device causes an ultrasound generating element to deliver ultrasound energy into the skin to thereby heat the affected area of the skin. In a preferred embodiment, the ultrasound generating element operates at a frequency of greater than 5 MHz and delivers ultrasound energy below the skin surface to heat tissue to a peak temperature of less than 70° C. in less than 20 seconds. The total heat transferred is low enough to prevent burns, typically less than about 50 J/cm$^2$ and for most applications less than about 5 J/cm$^2$.

The devices described herein utilize ultrasound energy, heat energy, or a combination of the two for killing bacteria. The devices described herein may also utilize ultrasound energy, heat energy, or a combination of the two for selective tissue heating that allows the user to achieve temporary pore enlargements for cleaning of the skin pores and expulsion of unwanted debris and undesired substances filling the pores, thus reducing the size of unseemly pores and enhancing the health and appearance of the skin.

The device described herein is also designed to allow treatment of the skin more effectively with possibly lower doses of rejuvenating agents. The device described herein is also designed to allow treatment of the skin more effectively by using ultrasound energy to improve penetration of rejuvenating agents (e.g. vitamins, botanicals, pharmaceuticals).

The method also contemplates ultrasound energy and/or thermal energy deposition into the skin to allow selective injury to the upper layers of the skin and new, more elastic collagen production. Not intending to limit the mechanism of action, it is believed that the controlled damage to the epidermis and upper layers of the dermis result in new collagen production and dual action via the use of a combined thermal heating and ultrasound absorption.

The disclosed compact hand held devices can be safely used by adolescents and adults wishing to improve the texture and appearance of their skin and to minimize the appearance of acne, blemished skin, or fine wrinkles. In one embodiment, the invention is a hand held device that can be used safely to heat a controlled layer of the skin to allow skin rejuvenation and collagen regeneration without collateral damage to adjacent tissue and while enhancing skin condition and appearance. The total heat energy transferred is low enough to prevent burns, typically less than about 50 J/cm2 and for most applications less than about 10 J/cm2.

When heat is used in the treatment of skin conditions, the heat may be applied in a pulsing or a non-pulsing manner. Preferably, the temperature used in the treatment is greater than about 45° C. The preferable range of temperatures is from about 40° to about 80° C. In a preferred embodiment, the high temperatures disclosed herein can be applied to the skin without causing burns as the temperatures are applied for short periods of time, preferably for less than about 1 second. The temperatures described herein could be the peak temperature achieved by the device on the skin surface or could be the peak temperature in the tissue below the skin surface at the application site. Preferably the peak temperatures achieved are greater than about 40° C., greater than about 45° C., greater than about 50° C., greater than about 55° C., greater than about 60° C., greater than about 65° C., greater than about 70° C., greater than about 75° C., greater than about 80° C., greater than about 85° C., greater than about 90° C., greater than about 95° C.

The preferred time for achieving the peak temperature with heat in both the pulse and/or non-pulse applications is from about less than about 1 second to about 60 seconds. Preferred times includes about 1 second, about 2 second, about 5 second, about 10 second, about 20 second, about 30 second, about 40 second, about 50 second, about 60 second, about 120 second.

When the device is applied to the skin the piezoelectric element is preferably allowed to cool before another application is made to the skin. Preferably, the element is cooled to about less than about 20° C., less than about 25° C., less than about 30° C., less than about 35° C., less than about 40° C., less than about 45° C., less than about 50° C., less than about 55° C., less than about 60° C. The time period for maintaining the cooled temperature is preferably about 5 seconds. Preferred time periods also include less than about 5 seconds, less than about 4 seconds, less than about 3 seconds, less than about 2 seconds, or less than about 1 second.

FIG. 1 shows a cross-sectional view of one embodiment of a hand held treatment device 10 suitable for use by a consumer. The dispenser may be powered by batteries 20. The circuit board 30 includes a microprocessor 35 (e.g. microchip PIC16F676) that accepts user input to control and deliver treatment. Being a hand-held device, the device 10 has an ergonomically shaped housing for the elements of the device 10. The device may be activated by depressing a button 40 located on the surface of the housing. The button 40 when depressed activates ultrasound drive electronics 45 that power an ultrasound transducer 50 located at the tip of the device 10. When activated ultrasound energy is produced for a preset treatment time typically less then 30 seconds. An optional infrared temperature sensor 55 monitors the temperature of the ultrasound transducer and can be used to control treatment and use. Alternatively, a thermocouple or other contact temperature sensor could be used.

Figure 13:
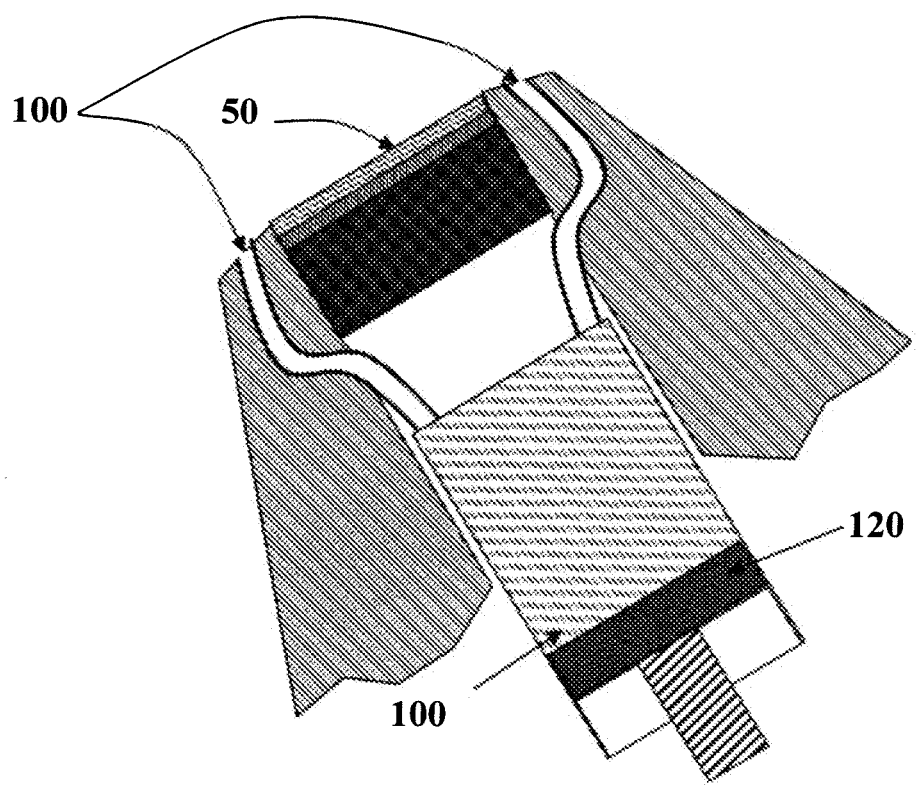
FIG. 13 is a cross-sectional view of the device of FIG. 1 showing a dispenser for dispensing a fluid near a transmitting end of the device.

In some embodiments the device includes a dispenser for dispensing a liquid or gel near the transmitting end of the device. This dispenser may be used to remove any air gaps between the skin surface and the surface of the transducer element 50. In some embodiments the dispenser may serve a dual role of acoustic coupling and providing a therapeutic agent directly into the pores of the skin as part of the ultrasound skin treatment. For example, with reference to FIG. 13, a transmitting end of the device of FIG. 1 includes fluid dispensing channels 100 to fill the gap between the ultrasound element 50 and the skin when the device is placed against the skin for treatment. The channels or tubes 100 are in fluid communication with a reservoir 110 for dispensing the fluid when a user or device activated pump 120 is actuated.

Figure 8:
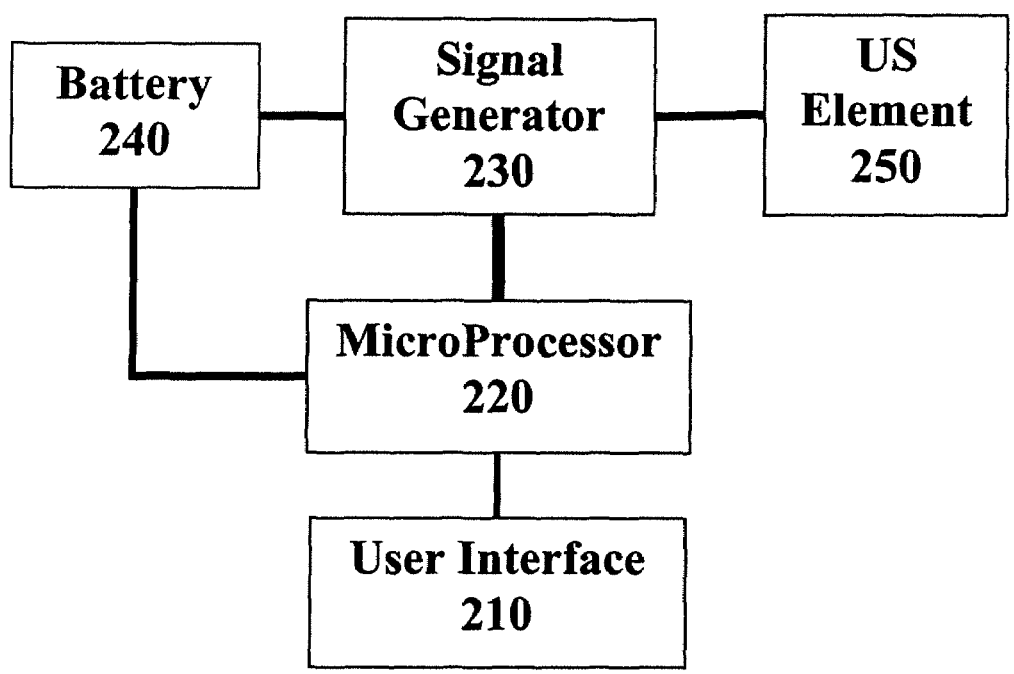
FIG. 8 shows a block diagram for an ultrasound device that uses a microprocessor.5656

Referring to FIG. 8, a schematic illustration of operational elements for device 10 is shown. A user interface 210 controls the operation of the device 10, an ultrasound transducer 250 transmits ultrasound energy when excited by a driving signal produced by a signal generator 230, which is powered by a battery 240. A microprocessor 220 controls the operation of signal generator 230 based on input from the user interface 210 and may conduct other functions as well, such as monitoring the temperature at the ultrasound element 250.

User interface 210 provides an interface for a user to activate the device (via button 40) and may also include a status LED indicator, mode selector and audio signals to indicate when a treatment is complete. In normal use the front surface of the ultrasound transducer 50 is pressed up against skin and the treatment button 40 pressed to deliver treatment. When the treatment is completed the device generates a sound, e.g., a buzzing sound, to indicate that treatment has completed. The user interface 210 may include buttons, switches, or touch screens for selecting operating modes of the device and to generate the continuous drive voltage that excites the piezoelectric.

In one embodiment the user can select different power levels or multi-pulse heating formats. An additional push button could be used to power the device and select operating modes. For example, pressing the button turns on the device at a low setting, pressing it again changes to high power setting, pressing it a second time changes to a multiple pulse heating format. Each time the button is pressed it cycles through all the possible modes. The current mode can be displayed by a series of LED's or a small LCD.

The signals from the user interface 210 are received by microprocessor 220 (e.g. PIC16F676 by Microchip inc.) that controls the functions of the drive signal generator 230. The drive signal generator 230 may be pre-set for a specific driving frequency based on the ultrasound element (or transducer) 250, or may be tunable among various driving frequencies. A feedback mechanism (not depicted) may be used to align or tune the driving frequency with the resonance frequency of the transducer. This process may also be controlled by the microprocessor 220. The signal generator 230 applies a sinusoidal or square wave voltage across a piezoelectric element. According to the preferred embodiment, the driving frequency is matched to an odd-harmonic of the piezoelectric element's resonance frequency.

According to other embodiments, an ultrasound device may be constructed that is simpler in design and may not require a microprocessor. According to these embodiments, the signal generator is preset to run for a fixed time period, and its driving frequency tuned to the manufactured piezoelectric and backing layer at the point of assembly. Thus, the signal generator and piezoelectric are preset to deliver a fixed amount of thermal energy for every treatment according to a preset driving frequency. As a safety precaution, a thermo-couple may be used to break the circuit if the temperature exceeds an amount that might lead to skin burns. According to this embodiment, the user interface may have only an on-off button that activates the ultrasound, and an LED or audio signal to indicate that the device is activated or that a treatment has finished.

Ultrasound transducer 250 is used to deliver ultrasound energy to the target site in the skin. The operating frequency for transducer 250 is typically within the range of 5 MHz to 100 MHz. In some embodiments, the transducer is configured so that it can efficiently deliver high frequency (preferably, >10 MHz) and high power ultrasound energy for a hand-held device that a consumer can use. Moreover, the transducer is rugged enough so that it is not susceptible to damage, e.g., as when operated by an adolescent for treating acne.

Figure 2:
FIG. 2 shows a sectional view taken through one embodiment of an ultrasound generating element, which uses air as a backing medium.

FIG. 2 shows one example of a transducer 60, a thin piezoelectric element 60 (e.g. PZT, or polyvinylidene fluoride (PVDF)). For efficient ultrasound generation the thickness of the piezoelectric element 60 should be half the wavelength ($\lambda$) of the driving frequency wavelength from the signal generator 230. For PZT and sound speed of 4170 m/s the thickness, t, for a 15 MHz driving frequency would be $$t = \frac{\lambda}{2} = \frac{c}{2f} = \frac{4170}{30 \times 10^6} = 139\,\mu m$$

The problem with operating the piezoelectric element at this fundamental resonance frequency is that the element's thickness is thin and consequently fragile. However, a thicker and, therefore more rugged element 60 may be used if the element 60 is tuned to an off-harmonic, preferably the third harmonic. At the third harmonic frequency (5 MHz) the thickness of the element 60 is three times that of the primary resonance frequency (15 MHz), i.e., 417 µm. In other embodiments, the thickness may be tuned to the $5^{th}$, $7^{th}$, $9^{th}$ etc. off-harmonics with a corresponding increase in the thickness of the piezoelectric element 60.

Figure 3:
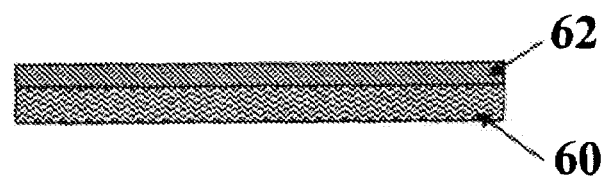
FIG. 3 shows a sectional view taken through another embodiment of the ultrasound generating element, which includes a thin impedance matching layer.

FIG. 3 shows an alternative transducer design that adds a matching layer 62 to the front surface of the piezoelectric element 60. The matching layer 62 is typically a quarter wavelength thick and has a characteristic impedance that is the geometric mean of the piezoelectric element and body tissue. A matching layer 62 may improve the transmission of the ultrasound into the tissue. A detailed discussion of matching layers may be found in "The Physics of Medical Imaging" Ed. Steve Webb (1988) incorporated herein by reference, and "Ultrasound in Medicine" Ed. F. A. Duck, A. C. Baker, H. C. Starritt (1997).

Figure 4:
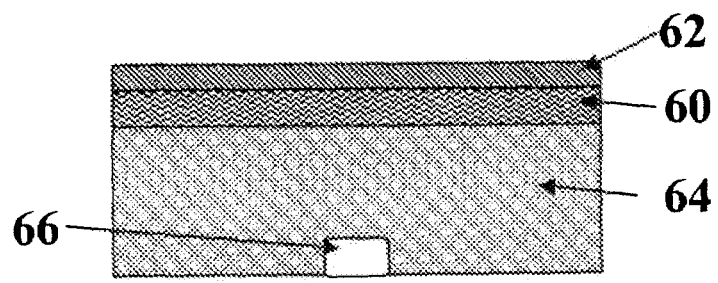
FIG. 4 shows a sectional view taken through another embodiment of the ultrasound generating element, which includes a thin impedance matching layer and backing layer with integrated temperature sensor.

FIG. 4 shows an alternative transducer design that adds a supporting backing layer 64 to the piezoelectric element 60. Unlike pulsed imaging transducers that use an absorbing backing layer, this design uses a low density polymer or foam to minimize the amount of ultrasound energy that is radiated into the backing layer. The matching layer 62 is optional. This design can integrate a temperature sensor 66 that is monitored and used to guide treatment. An integrated temperature sensor is an alternative to a non-contact infrared temperature sensor that can be integrated into the device.

Figure 5:
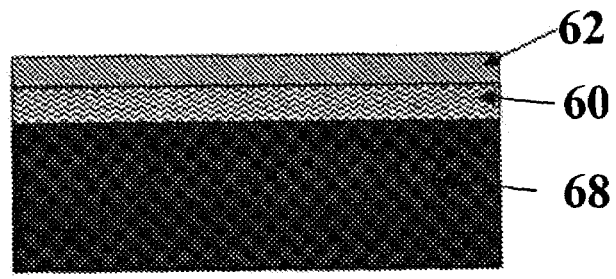
FIG. 5 shows a sectional view taken through another embodiment of the ultrasound generating element, which includes a high thermal conductivity backing layer.

FIG. 5 shows an alternative transducer design that uses a high thermal conductivity backing layer 68. Any high thermal conductivity material can be used including copper, brass, aluminum, silver, and gold. However, in order to efficiently radiate ultrasound energy [sound energy] from the front surface of the transducer, the backing layer 68 is acoustically matched according to the operating characteristics of the piezoelectric element 60. The thickness of the backing layer 68 is adjusted to be ($N\lambda + \lambda/4$) where $\lambda$ is the ultrasound wavelength at the operating ultrasound frequency as measured in the backing layer (e.g. for copper, and ultrasound frequency of 15 MHz, N=5, the thickness is approximately 1.25 mm).

An accurate thickness is essential to produce efficient ultrasound transmission from the front surface of the transducer. The backing layer 68 can be bonded to the piezoelectric element using ultrasonic welding, soldering, or epoxy. The thickness of the bonding layer should be less then about $\lambda/10$ to reduce acoustic losses and shifts in the resonance frequency. The thickness of the resonant backing layer 68 could be adjusted by small amounts $\delta$ to account for the effects of intermediate thin layers, such as an adhesive layer.

Figure 10:
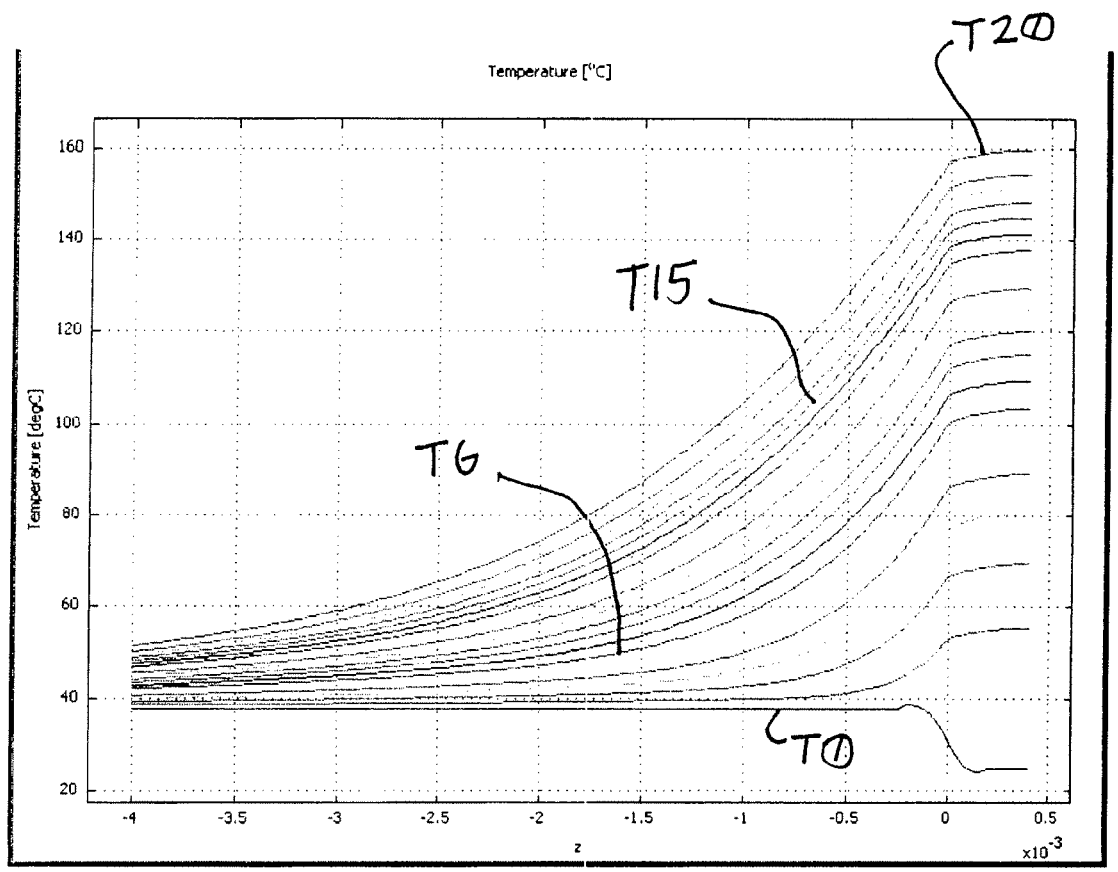
FIG. 10 shows the calculated temperature profile in the transducer and tissue during a treatment procedure using a single element ultrasound generating element (FIG. 2).
Figure 11:
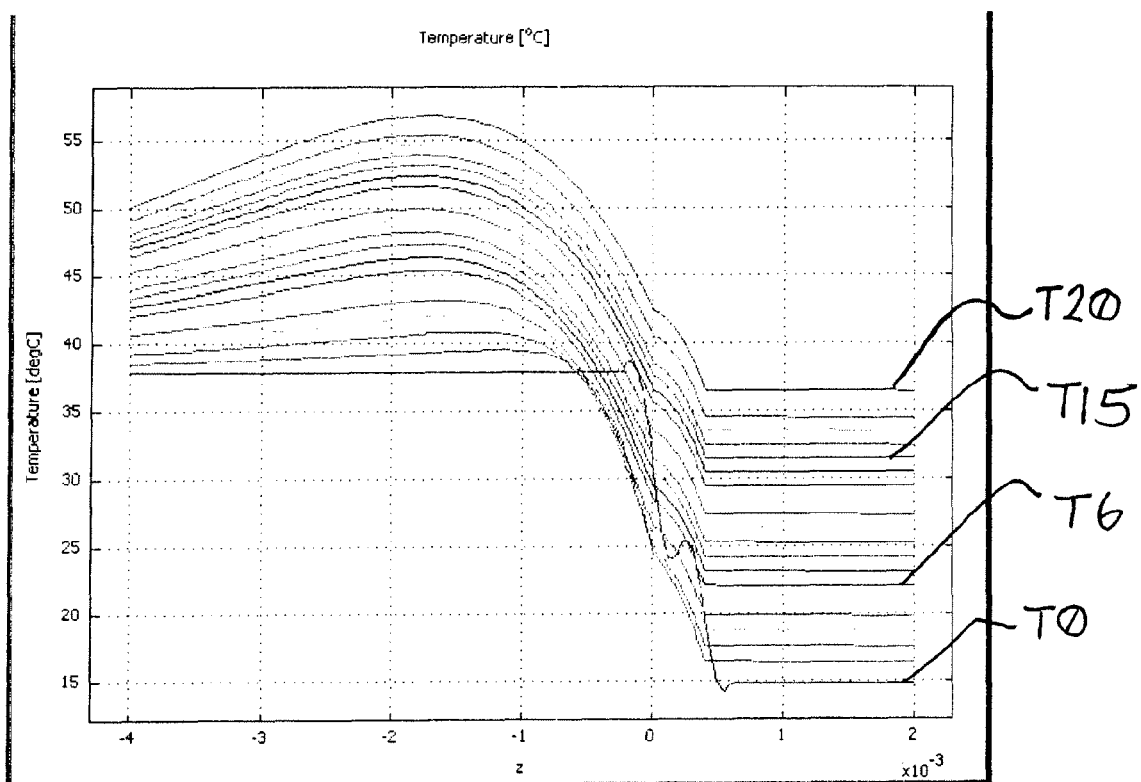
FIG. 11 shows the calculated temperature profile in the transducer and tissue during a treatment procedure using an ultrasound generating element with a high thermal conductivity backing layer (FIG. 5).

The role of the high thermal conductivity backing layer 68 is to conduct heat away from the piezoelectric element 60 and the skin. In one embodiment of the device this backing layer 68 is air cooled to improve cooling of the piezoelectric element 60. Alternatively, a thermoelectric cooler could be coupled to the backing layer 68 to further lower the piezoelectric element temperature. As is shown in FIGS. 10 and 11 cooling can significantly reduce the skin surface temperature and allow more ultrasound energy to penetrate the skin without risking a burn at the skin surface. The matching layer 62 is optional.

Figure 6:
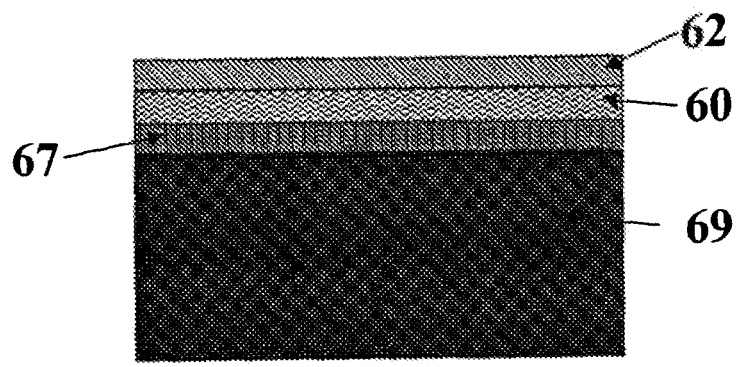
FIG. 6 shows a sectional view taken through another embodiment of the ultrasound generating element, which includes a matching layer between the ultrasound generating element and the high thermal conductivity backing layer.

FIG. 6, shows an alternative transducer design that includes a matching layer 67 between the piezoelectric element 60 and a thick high thermal conductivity backing layer 69. The thickness of the matching layer 67 should be $\lambda/4$ where $\lambda$ is the ultrasound wavelength at the operating ultrasound frequency as measured in the matching layer 67 (e.g. for aluminum, and ultrasound frequency of 15 MHz, the thickness is approximately 0.18 mm). The matching layer 67 should have a characteristic impedance which is the geometric mean of the piezoelectric element 60 impedance and the backing layer 69 impedance. A matching layer 67 may be desirable when the impedances of the piezoelectric element and high thermal conductivity backing layer 69 are significantly different. For an aluminum matching layer 67 a suitable backing layer 69 material is copper. For this design the backing layer thickness should be thick enough to provide total damping of the ultrasound. The matching layer 62 is optional.

In some embodiments, the ultrasonic energy transmitted from the forward or front surface of the ultrasound element uses a matching layer that does not focus ultrasonic energy. In these embodiments, the ultrasonic energy transmitted may be thought of as planar, uniform or non-focused. The emitted sound waves do not converge so as to increase the total amount of energy delivered to a specific area. Instead, all areas at the same depth beneath the transmitting end of the device are subjected to approximately the same amount of ultrasonic energy. Examples of these embodiments include devices that have an ultrasound element as shown in FIGS. 1-6.

In some embodiments a non-focused transmitting end is preferred for a consumer operated device because this can make the treatment of a skin condition simpler and safer to use by a consumer. When focusing elements are used, there may be a concomitant need to constantly re-position the device about the skin during a treatment session in order to effectively treat specific areas associated with a skin condition. That is, when the ultrasonic energy is focused, the treated area is small which can require that the device be moved about to treat a larger area. Also, when the ultrasonic energy is focused, there is a greater risk that misuse could lead to ultrasound focus occurring at the skin surface which could lead to a burn of the surface of the skin.

Figure 7:
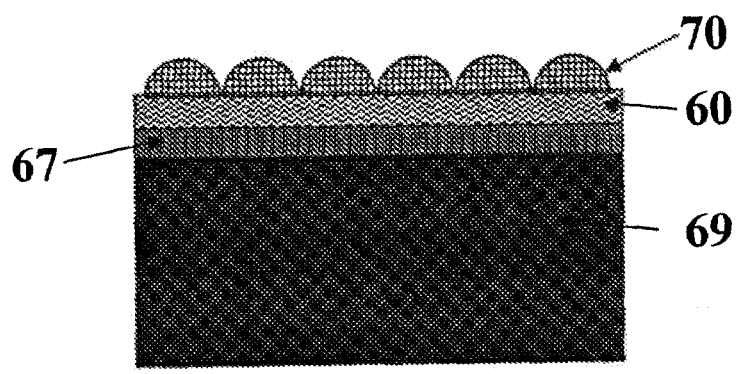
FIG. 7, shows an alternative transducer design that includes an array of ultrasound focusing lenses that can be used to produce a line or grid of heated tissue.

In other embodiments, lenses or focusing elements may be used to focus ultrasonic energy in one region of the skin. FIG. 7, shows an alternative transducer design that includes a line or array of ultrasound focusing lenses 70 that can be used to focus ultrasound energy so as to produce a line or grid of high intensity beams. This lenses can heat small regions of tissue (approximately 100 micron in diameter) to higher temperatures (e.g., >60 C), which can produce tissue damage for stimulating tissue repair and ultimately reduce wrinkles. Because each of the damaged areas within the grid are surrounded by undamaged tissue the healing can occur faster.

In order to get efficient ultrasound transmission into the skin it is necessary that the air gap between the transducer surface and the skin is completely filled with a fluid, or ultrasound gel. In one embodiment of the device the tip integrates a plurality of openings that are connected through an electronic valve to a fluid reservoir. When the device is placed on the skin and activated the valve opens for a fraction of a second to eject fluid or gel to fill the gap between the transducer surface and the skin. A replaceable cartridge within the device acts as a fluid reservoir. The fluid can be water, ultrasound gel, or therapeutic lotions. This embodiment eliminates the need by the user to apply water, gel, or cream to the tip of the device or skin surface before applying the device.

In one embodiment, a piezoelectric element with integral heat sink that can efficiently generate ultrasound energy of 5 MHz or higher may be assembled according to the following approach. First, a high piezoceramic element, e.g., TR300 High Density (PZT 8), produced by TRS Technologies, is cut to a desired size, e.g., 6 mm diameter, and thickness consistent with the desired fundamental resonance frequency, e.g., the third harmonic of 15 MHz or 5 MHz. Next, both sides of the piezoceramic are coated with a conducting electrode, e.g., electroless Nickel electrodes with or without an Immersion Gold coating. Optionally, electrodes may be extended at the sides of the element to facilitate attaching wires to the side rather than to transmitting surface. This can be done for both or just one electrode. Next, wires are bonded by soldering, ultrasonic welding or conductive epoxy. A fundamental resonance frequency is measured for this structure. Finally, a backing layer 68/69 is matched to the element's measured fundamental resonance frequency. That is, the thickness of the backing layer 68/69 is adjusted to be $(N\lambda+\lambda/4)$ where $\lambda$ is the ultrasound wavelength at the operating ultrasound frequency as measured in the backing layer (e.g. for copper, and ultrasound frequency of 15 MHz, N=5, the thickness is approximately 1.25 mm). The backing layer 68/69 may have a surface area over its thickness that matches that of the piezoelectric element, or the backing layer 68/69 may include a ledge for mounting the piezoelectric to the housing of the handheld device.

In one embodiment the exact resonance frequency of the piezoelectric element is determined automatically by the control electronics. In this automatic calibration the control electronics varies the drive signal frequency over a preset range that covers the expected possible resonant frequency of the piezoelectric element. The resonant frequency can be identified by detecting the maximum oscillation amplitude or alternatively by detecting the change in the characteristic circuit impedance. An automatic calibration technique allows low cost manufacturing techniques to be used to produce the piezoelectric element. For example, in order to make a low cost and easily adjustable circuit design a programmable clock oscillator, e.g., ECS-P55 may be used for tuning the signal generator to the ultrasound element's resonance frequency. Another option would be to select among several oscillators, e.g., 14.7-15.3 MHz, to use for each device, depending on the resonance frequency of the specific ultrasound element manufactured for the device.

FIG. 10 shows the calculated temperature profile from 0 to 20 seconds when a simple single piezoelectric element is used (FIG. 2). The vertical axis denotes the temperature in degrees Celsius and the horizontal axis the skin depth. The surface of the skin is at 0 meters and the transducer extends from $0.5 \times 10^{-3}$ to 0 meters. The multiple curves plot the predicted temperature at each Z location over a period of 20 seconds. Thus, T0 is the starting temperature at t=0 sec, T6 is the temperature at t=6 seconds, T15 for t=15 seconds, T20 for t=20 seconds, etc. The tissue extends from 0 to $-4 \times 10^{-3}$ meters. As the piezoelectric vibrates, it generates heat. As shown, peak temperatures are generated at the skin surface due to both ultrasound energy and thermal energy from the transducer.

FIG. 11 shows a similar calculation for the transducer design of FIG. 5 that uses a high thermal conductivity backing layer. In this case the peak temperature occurs at about 2 mm below the skin surface because thermal conduction into the pre-cooled high thermal conductivity backing layer reduces thermal conduction of the generated heat into tissue. The transducer is placed against the skin (z=0) and has a thickness of about ½ millimeter. It is seen that the transducer has a temperature gradient of about 10 degrees Celsius from front to back. The backing layer, due to its thermal mass, acts as a heat sink for heat generated by the piezoelectric. Thus, as heat is generated by the vibrating piezoelectric, the surface of the piezoelectric in contact with the backing layer is cooler than the opposing surface. This can lower the overall temperature at the surface of the skin (z=0) to below a burning temperature while, at the same time, effectively heating the skin below the surface by absorbed acoustical energy.

Controlling the tissue temperature is important to preventing skin burns. Henriques (F. C. Henriques, "Studies of Thermal Injury: The Predictability and the Significance of Thermally Induced Rate Processes Leading to Irreversible Epidermal Injury", Archives of Pathology, 43, 5 May 1947, Pages 489-502) published a theory on skin burns based on a form of the Arrhenius equation for heat induced irreversible chemical reaction. Although numerous other studies have investigated the burn process, the conclusions are similar. A skin burn occurs as a result of thermally induced changes in protein structure that have an activation energy of about 600 MJ/kg-mol. For skin the Henriques Integral equation can be written as:

$$\omega = \int_0^t e^{226.78 - \frac{75000}{T(t)}} dt$$

T is the temperature in Kelvin at depth x and is a function of time, and ω is a function of burn injury. Integration is carried out over the time the basal layer temperature is greater then or equal to 44° C. Second degree burns occur when ω=1. First degree burns occur for values of ω=0.53. Third degree burns occur at a critical value of ω=1 at the base of the dermis. Preferably, under normal operation, ω<0.4 for depths greater than 100 μm below skin surface using a short treatment time (typically less than 30 seconds). A high thermal conductivity backing layer can minimize any risk of a burn.

Figure 12:
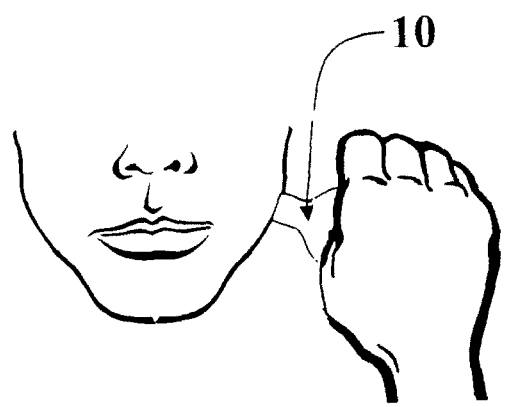
FIG. 12 shows how the device might be used to treat a blemish on the face.

FIG. 12 depicts how device 10 may be used to treat a blemish on the face. The device 10 is activated and then placed in contact with the skin. When the device 10 is in good contact and fully charged, a "fire" button is pressed to deliver energy to the ultrasound element, which then transfers ultrasound energy into the skin. The resulting heating of the skin acts to open pores and accelerate clearing of the blemish.

According to some methods of treatment, a topical agent is applied before device 10 is applied to the skin as shown in FIG. 12. For example, the topical agent may be applied by hand or the agent may be first applied to the tip or the ultrasound transmission end of the device 10 and then placed in contact with the skin when the device is placed against the skin as shown in FIG. 12. In other methods, the agent is applied after the ultrasound treatment. Applying the topical agent (or drug) at the target site, and then placing the transmitting end of the device 10 (e.g., surface of ultrasound element 50 or a matching layer) against the treated skin prior to treatment may improve results. The topical agent, being in a liquid form, can act as an acoustic coupling medium for improving sound transmission (i.e., the liquid eliminates air pockets between the skin and transducer surfaces). Ultrasound treatment while the agent or drug is on the skin may also cause the agent or drug to penetrate deeper into the affected pores thereby improving its effectiveness. Topical agents may include topical gels or creams, e.g., a topical gel with benzoyl peroxide for treatment of acne. Such agents may be applied before or after treatment with the device. Preferably, the area to be treated is first washed with mild soap or cleanser. After washing the area, the topical acne gel is applied and the device applied a minimum of one time to heat the target site. Then a topical acne gel may be applied again. This process may be repeated twice a day.

Figure 9:
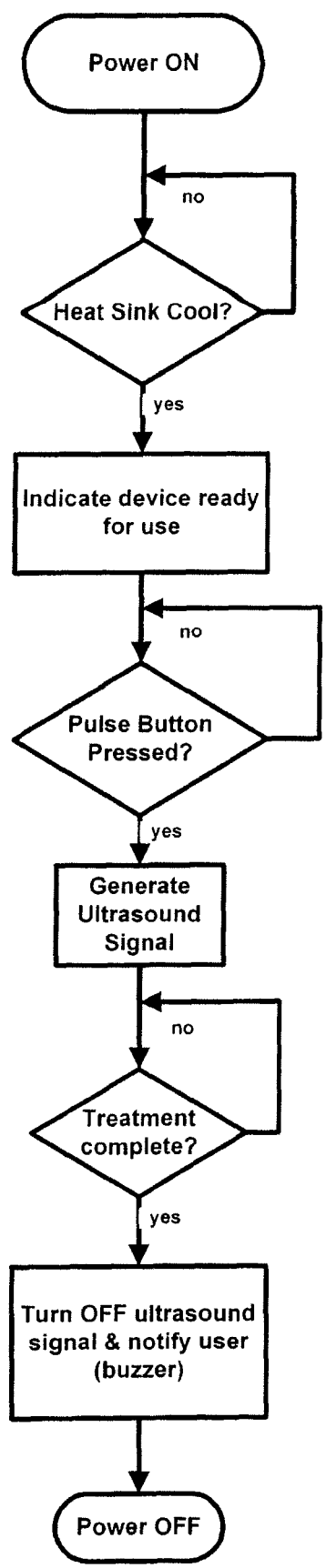
FIG. 9 is a flow diagram depicting a method of operation for the device of FIG. 1.

A flow process for device 10 according to one embodiment is depicted in FIG. 9. After the skin has been cleansed and a optical agent applied to the skin, the power is turned on. As part of an initialization routine, the device 10 may first check to see whether the backing layer or heat sink has reached a sufficiently cool temperature so that ultrasound treatment will not overheat the skin surface. During this time, a status LED may indicate this pending status by blinking, which indicates to the user that the device 10 is not yet ready for use.

The microprocessor 220 may periodically read a temperature sensed by a sensor coupled to the backing layer. After the microprocessor has determined that the backing layer has reached a temperature that should result in the temperature gradient depicted in FIG. 11 when the transducer is energized and placed against the target skin, the LED status ceases blinking. This indicates to the user that the device is ready for use. Alternatively, or in addition a thermocouple may be used to prevent transducer from being energized until the backing layer has fallen below a threshold temperature.

The control then senses whether the activating "pulse button" is depressed, which turns on the ultrasound signal generator. After the predetermined amount of time has elapsed, the ultrasound treatment ends and the user notified by a buzzer. The treatment period may by a single, continuous treatment period or a series of pulses as the user is depressing the button. Further, the treatment period or protocol may be selectable by the user, as discussed earlier.

In some cases, multiple treatments in one session may be necessary to effectively treat the blemish. In this case the minimum time between treatments may be controlled by a timer or sensed temperature monitored by a microprocessor. In a preferred embodiment, the device operates for a predetermined duration and then shuts off. The time interval in this case being selected so that the device delivers a pre-set amount of energy based on the operating frequency. In some embodiments, the total heat energy delivered is low enough to prevent burns at the skin surface, typically less than 50 J/cm² and for most applications less than about 5 J/cm².

Not intending to limit the mechanism of action—the present invention envisions a plurality of skin improvement effects by the methods of the present invention:

By depositing a controlled amount of ultrasound and thermal energy at the surface and allowing the energy to heat the upper layer of the dermis to achieve controlled damage to the collagen in the upper dermal layer.

By temporarily enlarging skin surface pores and allowing cleansing of the pores and causing expulsion of unwanted debris, dirt, and contaminants thus resulting in reduced pore size.

By temporarily enlarging skin surface pores thus allowing nutrients, conditioners, and possibly medications to flow into deeper layers of the skin.

By temporarily enlarging skin surface pores and allowing the expulsion of harmful sebum and bacteria thus reducing the chance for the development of acne and other sebaceous gland related ailments.

By thermally damaging the surface layers of the skin followed by flaking and removal of portions of the stratum conium, and portions of the epidermis and dermis.

By damaging a hair follicle and root using absorbed ultrasonic energy a reduction in hair growth is possible.

By thermally damaging vascular or a pigmented component of the skin near the skin surface (in the epidermis or upper dermis). These unwanted damaged components will then be removed by the body as waste products eliminating disfiguring skin blemishes.

The devices described herein are suitable for use in the treatment of various skin conditions and lesions. Examples of such skin conditions and lesions are provided herein, but are not limited to the conditions and lesions described herein. Bacterial and fungal skin infections lead to common lesions such as acne, pimples and under-nail fungal infections. Other lesions are caused by irritants, which may be introduced as a result of bug bites or by exposure to other natural or man-made skin irritants. Still other skin lesions are caused by viral infection, a common example being the lesions known as "cold sores" or "fever blisters."

Other skin conditions include pustular eruptions, localized abscessed formation and local inflammatory conditions of the dermis and epidermis. One of the most common afflictions of this type are lesion caused by the condition known as acne vulgaris. Acne vulgaris is associated with the Gram-positive anaerobic bacterium, *Propionibacterium acnes*. Abscess formation can also occur from a number of primarily bacterial species (commonly *Staphylococcus* and *Streptococcus*) as well as fungal species, such as dermatophytes.

A further type of skin lesions are viral skin lesions such as cold sores, also known as fever blisters. Cold sores are usually caused by strains of the Herpes Simplex virus and commonly result in lesions on and near the lips and inside the mouth of an infected individual.

A further type of skin lesion are fungal infections, also known as fungal dermatitis, including conditions known medically as Tinea corporis, Tinea pedis, Tinea unguium, Tinea capitis, Tinea cruris, and Tinea barbae. Particularly troublesome is the condition known as Tinea unguium which is a fungal infection occurring under toenails or fingernails, a condition also referred to medically as onychomycosis or ringworm of the nails. Onychomycosis may be caused by several types of fungi, including *Trichophyton mentagrophytes, Candida albicans* or *Trichophyton rubrum*.

Tinea corporis, also known as tinea circinata or tinea glabrosa and referred to generally as ringworm of the body, is a fungal infection or dermatophytosis of the glabrous skin, i.e., areas of skin other than bearded area, scalp, groin, hands and feet, generally caused by fungal species such as those of *Microsporum* such as *Microsporum canis, Trichophyton* such as *Trichophyton rubrum, T. Mentagrophytes*, and *Epidermophyton*, particularly by the fungal species of *Trichophyton* and *Epidermophyton*. The condition generally includes the presence of one or more well-demarcated erythematous, scaly mascules with slightly raised borders and central healing, producing annular outlines. Various other types of lesions may also occur, such as those that are vesicular, eczematous, psoriasiform, verrucous, plaque-like, or deep.

Tinea cruris, also referred to generally as "jock itch" or ringworm of the groin, is a fungal infection or dermatophytosis of the groin, perineum and perineal regions, generally seen in males, and sometimes spreading to contiguous areas, generally caused by fungal species such as those of *Microsporum, Trichophyton*, and *Epidermophyton*, particularly by the fungal species of *Trichophyton* and *Epidermophyton*. The condition generally includes severely pruritic, sharply demarcated lesions with a raised erythematous margin and thin, dry scaling. Tinea cruris often accompanies tinea pedis (also known as "athlete's foot").

Tinea pedis results in interdigital lesions. Athlete's foot is an itching, malodorous, uncomfortable disorder resulting from large numbers of ordinary, nonvirulent bacteria proliferating in the fungus infected interspace.

Certain insect bites and contact with certain plants can expose skin to irritants that result in an itchy or painful immune response. The symptoms generally manifest soon after the introduction of the irritant, but can persist or sporadically reoccur for extended periods of time when the irritant is not effectively removed or inactivated by the immune response.

The invention relates to methods and devices for the treatment of skin conditions and skin lesions involving the application of ultrasound and thermal energy to the infected or irritated tissue. The invention can be used to treat skin lesions caused by bacterial, fungal or viral infections through the application of an amount of heat. A skin condition or skin lesion that can be treated according to the present invention is any infected or irritated tissue that can be effectively treated by the application of heat.

The lesions can be the result of infection by a bacterial strain including but not limited to strains such as *Propionibacterium acnes, Staphylococcus* species or *Streptococcus* species. In preferred embodiments, the present invention provides methods and devices for the treatment of skin lesions such as the kind commonly associated with acne vulgaris. These skin lesions include pustular eruptions and localized abscesses such as cysts, nodules, pustules, papules, comedones (blackheads) and the like. These lesions include those that are commonly referred to as pimples, whiteheads, zits, acne and the like.

Alternatively or additionally, the lesions can further be result of infection by fungal species, including but not limited to fungal species capable of producing conditions such as toenail or fingernail infections, ringworm and the like. These fungal species include *Microsporum* species such as *Microsporum canis, Trichophyton* species such as *Trichophyton rubrum, Trichophyton. Mentagrophytes, Epidermophyton* species, *Candida albicans*, and the like. Such fungal species are sometimes referred to broadly as "dermatophytes".

Alternatively or additionally, in other embodiments, the skin lesions can be the result of viral infections, including infections caused by Herpes viruses such as Herpes simplex types I and II (cold sores and genital herpes), Varicella zoster (chicken pox) and the like.

Alternatively or additionally, embodiments of the present invention provide methods and devices for the application of ultrasound and heat for the treatment of skin lesions caused by an irritant. Common skin irritants that can be treated by the present invention include those introduced by bug bites, such as mosquito, chigger, ant, spider bites, scabies and the like. Other skin irritants introduced by other animal species, such as jellyfish, snakes and the like, or by plants such as poison ivy, poison oak, poison sumac and the like, can also be treated using the methods and devices of the present invention.

For the purposes of the present invention "treating" a skin lesion or condition means to slow, halt or even reverse the development of skin lesions or conditions and to reduce the lesion's or condition's healing time. Therapeutic benefit can be achieved by eradication or amelioration of the underlying disorder being treated, e.g., eradication or amelioration of the acne, and/or eradication or amelioration of one or more of the physiological symptoms associated with the condition being treated, notwithstanding that the patient may still be afflicted with the underlying disorder.

The above descriptions and illustrations are only by way of example and are not to be taken as limiting the invention in any manner. One skilled in the art can substitute known equivalents for the structures and means described. The full scope and definition of the invention, therefore, is set forth in the following claims.

What I claimed is:

1. A handheld ultrasound device for treatment of conditions visible on a skin surface, the device comprising:
   a signal generator configured to generate a driving signal having a frequency equal to or greater than about 10 Mhz;
   a piezoelectric element activated by the driving signal and when placed proximal to the skin surface configured to transmit planar ultrasonic waves through the skin for heating an area beneath the skin surface due to a uniform absorption of ultrasonic energy;
   a backing layer coupled to the piezoelectric element and configured to conduct heat away from the piezoelectric element and the skin,
      provide a temperature gradient across a thickness of the piezoelectric element, and
      maintain a temperature at the skin surface lower than a temperature beneath the skin surface; and
   a matching layer disposed between and contacting the backing layer and the piezoelectric element, wherein the matching layer has a characteristic impedance which is the geometric mean of the piezoelectric element impedance and the backing layer impedance.

2. The device of claim 1, further comprising a signal generator electrically coupled to the piezoelectric element for generating and transmitting the driving signal for activating the piezoelectric element, wherein the signal generator operates at an odd harmonic frequency of the fundamental piezoelectric frequency.

3. The device of claim 2, wherein the backing layer is configured to reduce a temperature of the piezoelectric element to about 25° C. before the driving signal is transmitted to the piezoelectric element.

4. The device of claim 2, wherein the driving signal is 15 MHz and the piezoelectric element includes a first thickness equal to about one-half the wavelength of a 5 MHz signal.

5. The device of claim 1, wherein the temperature gradient is at least 10° C./millimeter.

6. The device of claim 1, wherein the backing layer has a surface area matched to a surface area of the piezoelectric element.

7. The device of claim 1, wherein the backing layer comprises a high thermal conductivity material selected from at least one of copper, brass, aluminum, silver, and gold.

8. The device of claim 1, wherein the piezoelectric element is configured to have a temperature profile through the skin, such that the temperature is
   at a maximum at about 2 mm beneath the skin surface, and
   lower than the maximum nearer to the skin surface.

9. The device of claim 1, further comprising a layer of focusing lenses configured for being placed against the skin to focus ultrasound energy so as to produce high intensity beams.

10. The device of claim 1, further comprising:
   a housing for holding the signal generator, the backing layer, and the piezoelectric element, and including a gripping portion for holding the device in operative proximity to the skin, and
   a first switch for causing the signal generator to generate the driving signal, the switch being configured to be actuated while the housing is located in operative proximity to the skin,
   a second switch configured to select operating modes of the device,
   wherein a portion of the front surface is configured to be placed in contact with the skin.

11. The device of claim 10, wherein
   the driving signal has a wavelength corresponding to the frequency,
   the piezoelectric element tuned to the frequency has a first thickness with a first value, and
   the portion of the front surface has a second thickness with a second value that is at least three times higher than the first value,
   wherein the second switch is configured to cycle from one operating mode to a next operating mode of each of the operating modes of the device each time the switch is pressed.

12. The device of claim 1, the ultrasound device further comprising:
   a reservoir of gel or liquid; and
   a plurality of dispenser channels positioned around the piezoelectric element and in fluid communication with the reservoir and configured for dispensing a gel or liquid from the reservoir.

13. The device of claim 1, wherein the backing layer comprises one of copper or brass and the matching layer comprises aluminum.

14. The device of claim 1, wherein the backing layer is selected from one of a low density polymer and foam and configured to minimize the amount of ultrasound energy that is radiated.

15. The device of claim 1, wherein the backing layer comprises a thickness that is adjusted to be $(N\lambda+\lambda/4)$, where N is an integer and $\lambda$ is the ultrasound wavelength at the operating ultrasound frequency as measured in the backing layer.

16. A method for self-treating a skin condition using a hand-held device, the method comprising acts of:
   placing a piezoelectric element proximal to a skin surface, the piezoelectric element having a thickness, a backing layer coupled thereto to conduct heat away from the piezoelectric element and the skin and a matching layer disposed between and contacting the backing layer and the piezoelectric element, wherein the matching layer has a characteristic impedance which is the geometric mean of the piezoelectric element impedance and the backing layer impedance;
   transmitting planar ultrasonic waves through the skin for heating an area beneath the skin surface due to a uniform absorption of ultrasonic energy;

forming a temperature gradient across the thickness of the piezoelectric element when it is activated;

maintaining a temperature at the skin surface lower than a temperature beneath the skin surface; and emitting a sensory signal indicating an end to the self-treating.

17. The method of claim 16, further comprising an act of generating a periodic driving signal of about 10 MHz or higher and the piezoelectric element having a thickness about equal to $[(2N+1)/2] \lambda$, where $\lambda$ is the wavelength associated with the periodic driving signal and N is a non-zero integer.

18. The method of claim 16, further comprising an act of applying a topical agent to the skin before and after the self-treating.

19. The method of claim 18, wherein the topical agent is acne gel.

20. The method of claim 16, wherein the sensory signal is one of an audio or visual signal.

21. A method for therapeutic treatment of skin, the method comprising acts of:

providing an ultrasound device including a piezoelectric element, a backing layer coupled thereto to conduct heat away from the piezoelectric element and the skin and a matching layer disposed between and contacting the backing layer and the piezoelectric element, wherein the matching layer has a characteristic impedance which is the geometric mean of the piezoelectric element impedance and the backing layer impedance;

placing the piezoelectric element proximal to a skin surface;

transmitting ultrasonic energy of equal to or greater than about 5 MHz using planar ultrasonic waves for heating an area beneath the skin surface due to a uniform absorption of ultrasonic energy, the ultrasonic energy forming a temperature gradient across a thickness of the piezoelectric element; and maintaining temperature at the skin surface lower than temperature beneath the skin surface by the heating from the ultrasonic energy and the conduction of heat by the backing layer.

22. The method of claim 21, wherein a temperature profile through the skin has a maximum value at about 2 mm beneath the skin surface and decreases in magnitude nearer to the skin surface.

23. The method of claim 21, further comprising an act of maintaining a maximum temperature beneath the skin surface for about 20 seconds.

24. The method of claim 21, wherein the emission of the ultrasonic energy generates heat energy in an amount of less than about 50 J/cm$^2$.

25. The method of claim 24, wherein the heat energy is generated for a period of about 20 seconds.

26. The method of claim 21, wherein the heat energy is generated in an amount of less than about 5 J/cm$^2$.

27. The method of claim 21, wherein the act of transmitting ultrasonic energy heats the skin between a temperature of 40° C. and 85° C.

28. The method of claim 21, further comprising an act of maintaining a peak temperature for about 1 second to 60 seconds.

29. The method of claim 21, wherein the therapeutic treatment treats one of an acne vulgaris, viral skin lesion, skin irritant, and fungal infection condition using ultrasonic energy.

30. The method of claim 21, wherein the therapeutic treatment treats a hair follicle and hair root such that the absorbed ultrasonic energy damages the hair follicle and root to reduce hair growth.

31. The method of claim 21, further comprising an act of applying a substance to the skin.

32. The method of claim 31, wherein the substance comprises a topical agent.

* * * * *